(12) United States Patent
Wang et al.

(10) Patent No.: US 9,090,977 B2
(45) Date of Patent: *Jul. 28, 2015

(54) SILVER CATHODE ACTIVATION

(71) Applicant: Dow AgroSciences LLC, Indianapolis, IN (US)

(72) Inventors: Chen Wang, Midland, MI (US); Scott Lee Haynes, Saginaw, MI (US); Carey L. Scortichini, Midland, MI (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/906,663

(22) Filed: May 31, 2013

(65) Prior Publication Data

US 2013/0256148 A1    Oct. 3, 2013

Related U.S. Application Data

(63) Continuation of application No. 12/912,216, filed on Oct. 26, 2010, now Pat. No. 8,685,222.

(60) Provisional application No. 61/255,187, filed on Oct. 27, 2009.

(51) Int. Cl.
| | |
|---|---|
| *C25B 3/00* | (2006.01) |
| *C25B 3/06* | (2006.01) |
| *C25B 3/08* | (2006.01) |
| *C25B 3/04* | (2006.01) |
| *C07D 213/803* | (2006.01) |

(52) U.S. Cl.
CPC .............. *C25B 3/04* (2013.01); *C07D 213/803* (2013.01)

(58) Field of Classification Search
CPC .......... C25B 3/00; C25B 3/04; C07D 213/78; C07D 213/803

USPC ......................................... 205/426, 459, 460
See application file for complete search history.

(56) References Cited

U.S. PATENT DOCUMENTS

| | | | | |
|---|---|---|---|---|
| 4,217,185 | A * | 8/1980 | Kyriacou et al. | 205/426 |
| 4,242,183 | A * | 12/1980 | Kyriacou | 205/107 |
| 4,460,441 | A * | 7/1984 | Domning | 205/426 |
| 4,755,266 | A | 7/1988 | Bon et al. | |
| 6,352,635 | B2 | 3/2002 | Krumel et al. | |
| 8,685,222 | B2 * | 4/2014 | Wang et al. | 205/426 |
| 2001/0054559 | A1 * | 12/2001 | Krumel et al. | 205/341 |
| 2009/0090639 | A1 | 4/2009 | Wang et al. | |

FOREIGN PATENT DOCUMENTS

WO        2008042429        4/2008

OTHER PUBLICATIONS

Dyer et al., "The Silver/Silver-Oxide Electrode. II. Influence of a Superimposed Sinusoidal Potential on the Anodizing of Silver", Electrochimica Acta (no month, 1975), vol. 20, No. 2, pp. 161-171.*
International Searching Authority, International Search Report for PCT/US2010/054082, 2 pages, dated Dec. 21, 2010.
International Searching Authority, Written Opinion for PCT/US2010/054082, 6 pages, dated Apr. 27, 2012.
International Searching Authority, International Preliminary Report on Patentability for PCT/US2010/054082, 3 pages, dated Dec. 13, 2011.

* cited by examiner

*Primary Examiner* — Edna Wong
(74) *Attorney, Agent, or Firm* — Michael R. Asam; Faegre Baker Daniels LLP

(57) ABSTRACT

The selective electrochemical reduction of halogenated 4-aminopicolinic acids is improved by activating the cathode at a final potential from about +1.0 to about +1.8 volts.

6 Claims, No Drawings

SILVER CATHODE ACTIVATION

CROSS-REFERENCE TO RELATED APPLICATIONS

This application is a continuation application of U.S. patent application Ser. No. 12/912,216, filed Oct. 26, 2010, which claims priority to U.S. Provisional Application Ser. No. 61/255,187 filed Oct. 27, 2009, the disclosures of which are expressly incorporated herein by reference.

FIELD OF THE INVENTION

The present invention concerns an improved process of activating the silver cathode for the selective electrochemical reduction of halogenated pyridines and picolinic acids

BACKGROUND OF THE INVENTION

U.S. Pat. Nos. 4,217,185, 4,242,183 and 6,352,635 B2 and U.S. Patent Application Publication 2009/0090639 describe the preparation of certain halopyridine and halopicolinic acid derivatives by the selective electrochemical reduction of the corresponding higher halogenated pyridine and picolinic acid derivatives. In this process, the silver cathode is activated by an anodization that involves increasing the potential from an initial value of zero volts to a final value of at least +0.3 volts and preferably about +0.7 volts. Because of passivation, however, the reaction rate typically slows down as conversion proceeds and it is sometimes necessary to reactivate the cathode by re-anodization to finish a batch. It would be desirable to have an improved method for activating the cathode that is more resistant to passivation and would allow shorter reaction times.

SUMMARY OF THE INVENTION

It has now been found that, by activating the cathode at a final potential from about +1.0 to about +1.8 volts, the reaction rate is faster, and the cathode does not need to be reactivated as often to finish a batch. More particularly, the present invention concerns an improved process for the preparation of a 3-halopyridine or 3-halopicolinic acid of Formula I wherein X represents Cl or Br;

Y represents H, F, Cl, Br or $C_1$-$C_4$ alkyl, with the proviso that when X is Cl, Y is not Br;

$R^1$ represents Cl or $CO_2H$; and $R^2$ represents H or $NH_2$ in which a direct or alternating electric current is passed from an anode to a silver cathode through a solution of a 3,5-dihalopyridine or 3,5-dihalopicolinic acid of Formula II wherein X, Y, $R^1$ and $R^2$ are as previously defined, and wherein both of X are either Cl or Br, at a cathode potential of about −0.4 to about −1.7 volts relative to an Ag/AgCl (3.0 M Cl⁻) reference electrode, the improvement characterized by activating the cathode at a final potential from about +1.0 to about +1.8 volts, preferably about +1.2 volts.

This improvement is particularly advantageous for the production of 4-amino-3,6-diehloropyridine-2-carboxylic acid (aminopyralid) from 4-amino-3,5,6-trichloropyridine-2-carboxylic acid (picloram).

DETAILED DESCRIPTION OF THE INVENTION

The present invention concerns an improved process for the selective electrochemical reduction of the 5-halo substituent of a 3,5-dihalopyridine or a 3,5-dihalopicolinic acid. As used herein, the term "halogen" or "halo" refers to Cl or Br. Alkali metal means lithium, sodium, potassium, rubidium and cesium with sodium and potassium being preferred.

The reactions involved in the reduction of for example, a 4-amino-3,5-dihalopicolinic acid may be depicted as follows:

A) Neutralization:

B) Cathode Reaction:

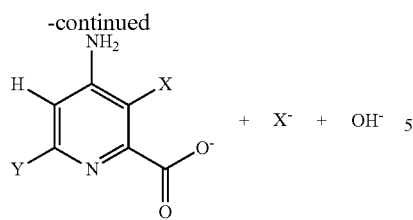

C) Anode Reaction:

2(OH$^-$)→½O$_2$+H$_2$O+2e$^-$

D) Overall Reaction:

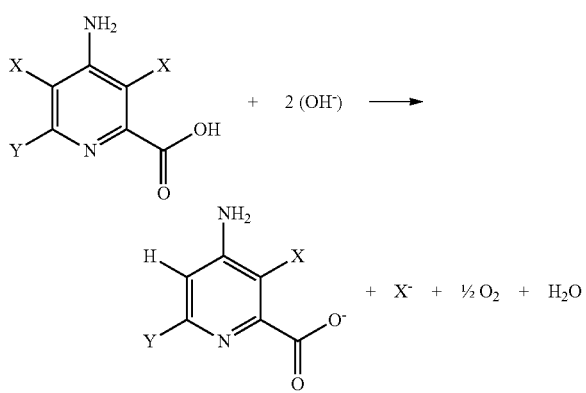

The carboxylic acid is recovered by acidifying the reaction mixture and recovering the product by conventional techniques.

The desired electrolytic reduction is carried out by techniques that are generally known in the art. In general, the starting material of Formula II is dissolved in a solvent to form an electrolyte which is added to the electrolytic cell while enough current is passed through the electrolyte until the desired degree of reduction is obtained.

It should be appreciated by those skilled in the art that the reduction potential of an aryl bromide is about 0.5 volt higher (less negative) than the comparable aryl chloride potential. The bromine will always be reduced off first. Thus, when X is Cl, Y cannot be Br.

The design of the electrolysis cell is flexible. The electrolysis can be conducted batchwise, or in a continuous or semi-continuous fashion. The cell may be a stirred tank containing the electrodes or a flow cell of any conventional design. In some cases, it may be desirable to employ a separator to divide the cell into separate anodic and cathodic compartments. Examples of useful separator materials are various anion and cation exchange membranes, porous Teflon, asbestos, and glass. While the use of three electrodes in which the potential of the cathode is controlled relative to a reference electrode is preferred, the electrolysis can alternatively be performed using only two electrodes, an anode and a cathode, and controlling either the cell current, the cell voltage, or both. For convenience, a 3-electrode undivided cell in which the electrolyte serves as both the catholyte and the anolyte is preferred.

The anode can be any chemically inert material including, for example, platinum, graphite, carbon, metal oxides such as silver, oxide on silver, or alloys such as Hastelloy C, with graphite, carbon and Hastelloy C being preferred. The cathode is primarily constructed of silver. Electrodes may be in the form of plates, rods, wires, screens, gauze, wool, sheets or pools, with expanded mesh screens being preferred. The anode or cathode may also consist of a coating applied to another material, an example of which is a noble metal oxide such as ruthenium oxide coated onto titanium.

The most preferred cathodes are activated silver cathodes prepared as described in U.S. Pat. Nos. 4,217,185 and 4,242,183. Such activated cathodes can be prepared by depositing a layer of silver microcrystals on a conductive substrate to form a composite electrode or by anodization of a silver electrode itself. For example, to illustrate the latter, an unactivated silver electrode can be dipped or immersed in an aqueous caustic catholyte solution and anodized, thus converting some of the silver at the surface of the electrode to silver oxide and roughening the surface at the same time. The polarity of the electrode is then reversed and the oxide electrolytically converted into particles of microcrystalline silver adhered to the surface of the electrode. The improved activation procedure of the present invention involves increasing the potential from an initial value of zero volts to a final value of at least +1.0 volts to about +1.8 volts, most preferably about +1.2 volts. Reduction of the oxide deposit requires negative polarization of the cathode. The cathode potential is gradually reduced from the value of about +1.0 to about +1.8 volts attained during the oxidation step, to a value of about −0.5 volts or less. It is not necessary to add any silver to the catholyte or aqueous base in this method.

Typically, the cathode is activated in the presence of from about 0.5 to about 4 wt % of an alkali metal chloride, bromide or sulfate, preferably NaCl, an excess of alkali metal hydroxide, preferably from about 1.0 to about 4.0 wt % NaOH, and the additional presence of the starting material to be reduced. Conveniently, the starting material is present in the same concentration as it is in the reaction feed, i.e., from about 1 to about 20 wt %, preferably from about 8 to about 12 wt %.

Water is the most preferred solvent for the electrolysis but, in some circumstances, it is possible to use an organic solvent either alone or as a co-solvent. The solvent or the co-solvent system should dissolve all or most of the starting material and the electrolyte, or at least enough to allow the reduction to proceed at a reasonable rate. In addition, the solvent or the co-solvent system should be inert to the electrolysis conditions, i.e., it does not detrimentally alter or react with the cathode or the catholyte materials to an intolerable extent. Other than water, preferred solvents/co-solvents are miscible with water and include lower molecular weight alcohols, ethers such as tetrahydrofuran, dioxane and polyglycol ethers, and lower amides such as dimethylformamide or dimethylacetamide.

Alkali metal hydroxides are needed as the supporting electrolyte and NaOH and KOH are the most preferred supporting electrolytes. While NaCl is the preferred salt, other salts can be used, including alkali chlorides, bromides, and sulfates.

In the reaction, one equivalent of base is required to neutralize the starting material in the case of a 3,5-dihalopicolinic acid, and an additional equivalent is required to generate hydroxyl ions that are consumed in the electrolysis. The reaction is typically conducted with an excess of base, preferably with a 1 to 4 weight percent excess of base throughout the reaction.

The concentration of 3,5-dihalopyridine or a 3,5-dihalopicolinic acid in the catholyte or feed can be from about 1 to about 20 percent by weight, preferably from about 8 to about 12 percent by weight. Lower concentrations 1 duce productivity while higher concentrations usually result in lower yields, lower product purity and lower electrical efficiencies.

Suitable temperatures for the electrolysis generally range from about 5 to about 90° C. The preferred temperature range is from about 20 to about 60° C. From about 30 to about 50° C. is most preferred.

One skilled in the art will appreciate that the apparent cathode potential at which the halogen will be selectively reduced is dependent on a variety of factors including, for example, the structure of the particular substrate, the cell configuration, and the distance separating the electrodes. In general, the cathode potential, relative to a standard Ag/AgCl (3.0 M Cl⁻) electrode, should be within the range of about −0.4 to about −1.1 volts for Br and within the range of about −0.8 to about −1.7 volts for Cl. For Br, the cathode potential is preferably from about −0.6 to about −0.9 volts. For Cl, the cathode potential is preferably from about −1.0 to about −1.4 volts. The current density in amperes per square centimeter ($amp/cm^2$) should be at least 0.005, preferably about 0.05 $amp/cm^2$ or greater.

While the evolution of molecular oxygen is preferred, many other anodic reactions can be employed. Examples include the evolution of molecular chlorine or bromine, oxidation of a sacrificial species such as formate or oxalate to give carbon dioxide, or the oxidation of an organic substrate to form a valuable co-product.

In the presently preferred mode of operation for a 3,5-dihalopicolinic acid, the starting material is dissolved in aqueous caustic brine to form a basic aqueous solution (e.g., ~10 wt % halogenated 4-aminopicolinic acid, ~2.5 wt % excess NaOH and ~1 wt % NaCl) which is continuously recirculated through an undivided electrochemical cell having an expanded silver mesh cathode activated by anodization at +1.2 volts in the presence of the feed solution. While keeping the reaction mixture alkaline, electrolysis at a cathode potential of from about −0.6 to about −1.5 volts relative to an Ag/AgCl (3.0 M Cl⁻) reference electrode is continued until the desired degree of reduction has occurred. The desired product is recovered by conventional techniques. For example, the acid can be precipitated from the reaction mixture by acidification followed by either filtration or extraction with a water immiscible organic solvent.

The following examples are illustrative of the present invention.

EXAMPLES

Preparation of 4-amino-3,5,6-trichloropyridine-2-carboxylic acid (picloram) feed solution To a 4-liter (L) flask was added 2420 grams (g) of hot water, 250 g of 50 percent by weight NaOH, 30 g of NaCl, and 300 g of picloram (95 percent). The solution was stirred for 30 minutes (min), filtered through a 1 micron polypropylene film, and transferred to a 5-L feed circulation tank. This solution weighed 3000 g and contained 9.5 weight percent 4-amino-3,5,6-trichloropyridine-2-carboxylic acid, 2.0 to 2.5 percent of excess NAM, and 1.0 percent of Nan. This feed solution was used in both the comparative example and the improved example for this disclosure.

Example A

Preparation of 4-amino-36-dichloropyridine-2-carboxylic acid with anodization at 0.7 volts (Comparative)

To an undivided electrochemical cell was added 500 g of the picloram feed solution. This feed solution was circulated at a rate of 4 Liters per minute (L/min) and a temperature of 43-45° C. through one undivided electrochemical cell. The size of the silver mesh electrode was 1.8 cm×15.4 cm. After normal anodization at +0.7 volts (V), the polarity of the cell was reversed and the electrolysis was started. The cathode working potential was controlled at −1.35 V relative to an Ag/AgCl (3.0 M Cl⁻) reference electrode. While recirculating the feed, a total of 10 mL of 50 percent by weight NaOH were added over the first 5 hours to maintain the NaOH concentration at 1.5-3.0 percent excess. The current started at 5.0 amps and slowly decreased to 0.6 amp at 24 hours.

No more anodization was needed after the electrolysis was started. At 8 hours, the cell effluent has 68% aminopyralid and 26% picloram (both in HPLC area %). At 24 hours, the cell effluent had 88% aminopyralid and 3.2% picloram.

Example 1

Preparation of 4-amino-3,6-dichloropyridine-2-carboxylic acid with anodization at ±1.2 volts To the same undivided electrochemical cell in Example A was added 500 g of the picloram feed solution. This feed solution was circulated at a rate of 4 L/min and a temperature of 43-45° C. through one undivided electrochemical cell. After normal anodization at +1.2 volts (V), the polarity of the cell was reversed and the electrolysis was started. The cathode working potential was controlled at −1.35 V relative to an Ag/AgCl (3.0 M Cl⁻) reference electrode. While recirculating the feed, a total of 10 mL of 50 percent by weight NaOH were added over the first 5 hours to maintain the NaOH concentration at 1.5-3.0 percent excess. The current started at 6.5 amps and slowly decreased to 0.7 V at 2.4 hours.

No more anodization was needed after the electrolysis was started. At 8 hours, the cell effluent had 76% aminopyralid and 17% picloram (both in HPLC area %). At 24 hours, the cell effluent had 88% aminopyralid and 1.2% picloram.

The invention claimed is:

1. A method for preparing a compound, the method comprising the steps of:
   activating a silver cathode by anodizing the cathode at a final potential in the range of +1.05 to +1.8 volts;
   passing a direct or alternating electric current from an anode to the activated silver cathode through a solution of 3,5-dihalopyridine or 3,5-dihalopicolinic acid of Formula (II)

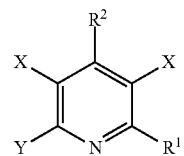

(II)

wherein:
X represents Cl or Br;
Y represents H, F, Cl, Br, or $C_1$-$C_4$ alkyl, with the proviso that when X is Cl, Y is not Br;
$R^1$ represents Cl or $CO_2H$; and
$R^2$ represents H or $NH_2$; and
forming a 3-halopyridine or 3-halopicolinic acid of Formula (I)

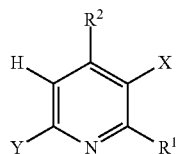

wherein
X represents Cl or Br;
Y represents H, F, Cl, Br or $C_1$-$C_4$ alkyl, with the proviso that when X is Cl, Y is not Br;
$R^1$ represents Cl or $CO_2H$; and
$R^2$ represents H or $NH_2$.

2. The method of claim 1, further including the step of reversing the polarization of the activated cathode.

3. The method of claim 1 in which the 3-halopicolinic acid of Formula I is aminopyralid and the 3,5-dihalopicolinic acid of Formula II is picloram.

4. The method of claim 1, wherein activating the silver cathode includes activating the silver cathode by anodizing the cathode at a final potential in the range of +1.1 to +1.8 volts.

5. The method of claim 1, wherein activating the silver cathode includes activating the silver cathode by anodizing the cathode at a final potential in the range of +1.2 to +1.8 volts.

6. The method of claim 1, wherein activating the silver cathode includes activating the silver cathode by anodizing the cathode at a final potential of +1.8 volts.

* * * * *